US010456292B2

(12) United States Patent
DePinto et al.

(10) Patent No.: US 10,456,292 B2
(45) Date of Patent: *Oct. 29, 2019

(54) COMPOSITIONS AND METHODS RELATING TO AN OCCLUSIVE POLYMER HYDROGEL (71) Applicant: Revolution Contraceptives LLC, Berkeley, CA (US)

(72) Inventors: Jeffrey T. DePinto, Perkasie, PA (US); David A. Templer, Dresher, PA (US); Antonina A. Nikitenko, Tarrytown, NY (US); Gary Gamerman, Vienna, VA (US); Donald P. Waller, Oak Brook, IL (US); David Bolick, Pittsburgh, PA (US); Elaine Lissner, Berkeley, CA (US)

(73) Assignee: Revolution Contraceptives LLC, Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/833,959

(22) Filed: Dec. 6, 2017

(65) Prior Publication Data
US 2018/0092769 A1 Apr. 5, 2018

Related U.S. Application Data (62) Division of application No. 14/517,796, filed on Oct. 17, 2014, now Pat. No. 9,861,515.
(Continued)

(51) Int. Cl.
A61F 6/20 (2006.01)
C08F 4/34 (2006.01)
(Continued)

(52) U.S. Cl.
CPC ............ A61F 6/20 (2013.01); A61L 24/0031 (2013.01); A61L 24/06 (2013.01); C08F 4/34 (2013.01); A61L 2430/36 (2013.01)

(58) Field of Classification Search
None
See application file for complete search history.

(56) References Cited

U.S. PATENT DOCUMENTS 2,621,169 A 12/1952 Robinette, Jr.
4,705,773 A 11/1987 Le-Khac
(Continued)

FOREIGN PATENT DOCUMENTS

JP 1989051415 A 2/1989
WO WO 1997/045131 12/1997
(Continued)

OTHER PUBLICATIONS

Ansari, et al.; "Evaluation of genotoxicity in leukocytes and testis following intra-vasal contraception with RISUG and its reversal by DMSO and NaHCO3 in Wistar albino rats"; (2013), Reproductive Toxicology, vol. 36, pp. 53-59.
(Continued)

Primary Examiner — Robert A Wax
Assistant Examiner — Melissa S Mercier
(74) Attorney, Agent, or Firm — DLA Piper LLP (US)

(57) ABSTRACT

Methods for the synthesis and use of several variations of styrene maleic acid-based polymers and the hydrogel tissue bridges that can be formed from such polymers. Specifically, a method is disclosed for synthesizing a styrene maleic acid-based polymer that can be dissolved in DMSO and injected into the vasa deferentia of male subjects, creating a hydrogel tissue bridge. This hydrogel tissue bridge can occlude the vas deferens, thus forming an effective male contraceptive. Additionally, this male contraceptive can be (Continued)

reversed by injecting the lumen of the vas deferens with a basic buffer solution to dissolve and remove the hydrogel tissue bridge.

14 Claims, 6 Drawing Sheets

Related U.S. Application Data

(60) Provisional application No. 61/892,404, filed on Oct. 17, 2013.

(51) Int. Cl.
*A61L 24/00* (2006.01)
*A61L 24/06* (2006.01)

(56) References Cited

U.S. PATENT DOCUMENTS

| | | | |
|---|---|---|---|
| 5,488,075 A * | 1/1996 | Guha | A61K 31/765 424/78.2 |
| 5,989,580 A | 11/1999 | Wallace et al. | |
| 6,103,254 A | 8/2000 | Wallace et al. | |
| 6,531,111 B1 * | 3/2003 | Whalen, II | A61K 49/0002 424/1.65 |
| 6,756,031 B2 | 6/2004 | Evans et al. | |
| 6,858,219 B2 | 2/2005 | Evans et al. | |
| 7,009,011 B1 | 3/2006 | Keoshkerian | |
| 9,861,515 B2 * | 1/2018 | DePinto | A61F 6/20 |
| 2009/0324537 A1 | 12/2009 | Bucevschi et al. | |
| 2011/0002979 A1 | 1/2011 | Guha | |
| 2011/0021729 A1 | 1/2011 | Ron et al. | |

FOREIGN PATENT DOCUMENTS

| | | | |
|---|---|---|---|
| WO | WO 1997/045131 A1 | 12/1997 | |
| WO | WO-9745131 A1 * | 12/1997 | ........... A61K 9/0024 |
| WO | WO 2000/045864 A1 | 8/2000 | |
| WO | WO 2000/054746 | 9/2000 | |
| WO | WO 2007-115165 A2 | 10/2007 | |
| WO | WO 2009/113108 | 9/2009 | |

OTHER PUBLICATIONS

Banerjee et al.: "Probing molecular interactions of poly (styrene-co-maleic acid) with lipid matrix. models to interpret the therapeutic potential of the co-polymer", Biochimica et Biophysica Acta, 1818, (2012), pp. 537-550.
Extended European Search Report dated Jul. 3, 2017, regarding EP 14853758.2.
Guha et al: "Designed Self Assembly of Nano-Liposomes in the Male Reproductive Tract for Model Drug Delivery to the Prostate"; Open Nanoscience Journal, 2011, vol. 5, pp. 1-5.
International Search Report in Counterpart PCT application, PCT/US2014/061272.
Jha, Rakhi K. et al.: "Smart RISUG: A potential new contraceptive and its magnetic field-mediated sperm interaction"; International Journal of Nanomedicine, 2009, vol. 4 pp. 55-56.
Japanese Office Action dated Jun. 19, 2018, regarding JP 2016-524519.

* cited by examiner

COMPOSITIONS AND METHODS RELATING TO AN OCCLUSIVE POLYMER HYDROGEL

CROSS-REFERENCE TO RELATED APPLICATIONS

This application is a continuation application of U.S. application Ser. No. 14/517,796 filed Oct. 17, 2014, now pending; which claims the benefit under 35 U.S.C. § 119(e) to U.S. Application Ser. No. 61/892,404 filed Oct. 17, 2013. The disclosure of each of the prior applications is considered part of and is incorporated by reference in the disclosure of this application.

BACKGROUND OF THE INVENTION

Field of the Invention

The present compositions and methods relate to the field of hydrogel tissue bridges for use in creating occlusions and related structures in the body.

Background Information

While long-term reversible contraceptives, such as IUDs and implantable time-released birth-control medications, have become popular methods for pregnancy prevention in females, comparable methods for males do not exist. Additionally, short-term reversible male contraceptives, such as male condoms, withdrawal and periodic abstinence have relatively high failure rates (Trussed J. Contraceptive failure in the United States. Contraception 2004; 70: 89-96) making them less than ideal solutions for male contraception. Furthermore, even these basic contraceptives may not be readily available or widely accepted by the populations of some countries. For these and many other reasons, a pressing need for long-term reversible male contraception currently exists, which has not yet been met.

To date, the only commonly available long-term male contraceptive method is vasectomy: a surgical procedure wherein the vasa deferentia of subjects are severed and cauterized, effectively preventing the passage of any sperm from the testes. Although a vasectomy is a highly effective measure of contraception, should the subject decide to undergo vasectomy reversal, known as a vasovasostomy, the cost to the subject can be very high and the procedure is not always successful.

Several attempts have been made to create an alternative to the vasectomy. Specifically, devices that block the vas deferens have been made of urethane and silicone plugs as well as injectable medical grade silicone and polyurethane rubber. These methods have been tested but have proven unsuccessful due to leakage and/or scarring (Tulsiani & Abou-Haila, 2008). Valves implanted into the vas deferens were also unsuccessful (See Hollander Published U.S. Patent Application US 2014/0048076). Intra Vas Devices have been tested in humans, including a urethane mesh plug using a flexible synthetic anchored to the vas wall (Song et al., 2006). However, this device proved less effective than vasectomy in Phase 2 clinical trials and has been abandoned.

The use of a styrene maleic-based polymer to create a long-term reversible male contraceptive has been previously disclosed. Specifically, Guha (U.S. Pat. No. 5,488,075 and U.S. Patent App. 2011/0002979) has disclosed a polymer for use in vasa deferentia, created from a solution of styrene maleic anhydride or mixtures comprising less than equal parts of styrene maleic anhydride and styrene maleic acid, with the majority being the anhydride. While Guha has claimed to have disclosed a form of male contraception that is both effective and reversible, it has not yet gained regulatory approval despite a multi-decade development process. The disadvantages of this method have been shown to exist both in the synthesis of the styrene maleic-based polymer and its use. Firstly, the synthesis of Guha's polymer calls for the use of gamma irradiation to initiate free radical polymerization of the styrene maleic monomers. The use of gamma radiation can be hazardous and is not convenient or practical for either widespread small-scale synthesis or large-scale manufacturing. Furthermore, Guha's method requires onerous purification steps that call for retorting, organic/aqueous crystallization/separation and other difficult manufacturing processes.

It is of critical note, and point of difference with the present invention, that Guha teaches a composition that is comprised of styrene maleic anhydride for injection. Although he describes that once injected into the body the anhydride residues convert to an acid (and which he asserts provide a stable charge and pH effect that deactivates the sperm), his teachings include that a product must contain maleic anhydride on injection to perform acceptably. The present compositions and methods are based almost entirely on styrene maleic acid rather than styrene maleic anhydride. This use of styrene maleic acid over styrene maleic anhydride is based upon critical inventive discoveries. It has been discovered that an anhydride is not easily stabilized in dimethyl sulfoxide (DMSO) due to residual water in commercially available DMSO (and its highly hygroscopic nature). The inability to stabilize the anhydride makes manufacturing, quality control and shelf-life difficult to manage, and could result in product at time of injection with variable and unpredictable viscosity and other characteristics. It has been observed that polymers with elevated anhydride, or entirely anhydride, formed harder, semi-rigid solids on injection that may present risk of complications to the patient until the plug can later convert to the soft gelatinous acid form. In our research, and in direct contradiction to the teachings of Guha, it has been presently determined that an acid-based polymer can easily be produced, which can be stabilized in DMSO and can have well-controlled quality and consistency required for an injectable medical product, while providing durable contraceptive function and handling characteristics. Moreover, upon injection, in direct contradiction to the teachings of Guha, the present compositions can readily form a soft, stable space-filling plug that can provide durable and reversible blockage to the passage of sperm. In sum, the present compositions and methods show that it is unnecessary—in fact unfavorable—to produce a "prodrug" anhydride-based polymer that would convert in vivo to the active agent. Rather the present disclosure proves that the acid form can be produced and directly used as an effective occlusion agent.

Guha's method creates a styrene maleic anhydride bulk having a molecular weight between 60-100 kilodaltons (kDa) with Guha's preferred range being between 70-80 kDa. The resulting styrene maleic anhydride bulk can be mixed with a lesser amount of styrene maleic acid bulk to form a mixed polymer. This mixed polymer is then added to DMSO to create an injectable solution, which can be introduced into the vas deferens via needle and syringe.

Interestingly, Guha does not teach the creation of an impenetrable occlusion. Rather, Guha believes that his polymer chemically inactivates sperm as it passes though openings in the injected polymer, due to charges created by a residue in the polymer containing both styrene maleic anhydride and styrene maleic acid. Specifically, Guha teaches that his polymer leaves open passages having a charged surface across which sperm cells must traverse and thereby become inactivated. While Guha may or may not be correct that his disclosed polymer has the ability to deactivate all of the sperm that passes through it, the formation of an occlusion in the vas deferens that prevents passage of all sperm cells through the vas deferens would eliminate the need for such chemical deactivation.

The field of male contraception does not have, and currently needs, a long-term reversible male contraceptive comprising a hydrogel tissue bridge that can create an occlusion within the vas deferens. The polymer required to create such an occlusion must have flow properties which allow it to fill small spaces and should set up as a plug that is impenetrable to sperm, while preferably still allowing the passage of other bodily fluids. It would be preferable that this plug remain soft and flexible to avoid damage to surrounding tissues and be more comfortable for the patient than would a rigid plug.

SUMMARY OF THE INVENTION

It is an aspect of the present disclosure to provide methods and compositions for the creation of a long-term reversible male contraceptive comprising a hydrogel tissue bridge that can create an occlusion within the vas deferens or other bodily lumens or cavities, the forming polymer having flow properties which allow it to fill small spaces and form a plug, which is impenetrable to sperm, while allowing the passage of other bodily fluids, and which remains flexible to avoid damage to surrounding tissues and be more comfortable for the patient.

This aspect can be attained by a hydrogel-forming solution comprising a polymer dissolved in a solvent, wherein the polymer is more than 75% comprised of styrene maleic acid and the solvent is DMSO.

This aspect can also be attained by a method for using a hydrogel-forming solution to create a hydrogel tissue bridge within a space located within a subject, wherein the hydrogel-forming solution can be placed within the space within a subject by an injecting apparatus and the hydrogel-forming solution can absorb the available water and aqueous solutions within the space to create a hydrogel tissue bridge within the space.

BRIEF DESCRIPTION OF THE DRAWINGS

Further features and advantages of the present disclosure, as well as the details of various embodiments of the present disclosure, will become apparent and more readily appreciated from the included drawings.

DETAILED DESCRIPTION OF THE INVENTION

This description of the exemplary embodiments is intended to be read in connection with the accompanying drawings, which are to be considered part of the entire written description.

The present disclosure relates generally to the selectively reversible formation, in a chosen region of the anatomy, of a semi-solid, hydrogel tissue bridge created by a special hydrogel-initiating/effecting solution, also referred to herein as a "hydrogel-forming solution." The hydrogel tissue bridge can be implemented via appropriate injection or other application of the hydrogel-forming solution to the anatomy. More specifically, the present disclosure pertains to several compositions proposed for such a hydrogel-forming solution, and to the readily scalable synthesis of these solutions. The term "tissue bridge" is employed herein to refer broadly to a structure—a solution-enabled/deposited material mass—which is attached to, and which spanningly connects, spaced regions in the anatomy, such as within, and fully, or substantially fully, spanning, an anatomical lumens, vessel, channel, cavity and bladder or similar structure. Invention-utility illustrations mentioned below each reside, as contemplated herein, in the category of being a "tissue bridge."

Anatomical hydrogel tissue bridging, such as that implemented by employment of the present hydrogel-forming solution, offers many useful anatomical applications, such as occluding/blocking (partially or otherwise), crevice/void-space or depot filling, and tissue bulking or coating, among other structural applications within the body. While uses of the solutions described herein will focus primarily on the field of occlusion-based male contraception, the present solutions have application in other anatomical structures, namely, other lumens of the body, channels, sinuses or cavities, which are all contemplated as being part of the present disclosure. For example, occlusion of the Fallopian tubes as well as occlusion of tubes, vessels, and/or ducts of the lymphatic, glandular, hepatic and renal systems are contemplated uses of the present hydrogel forming solution and the hydrogel tissue bridge formed from it. The present compositions and methods can also be used as a biocompatible space filling tissue bridge or bulking agent when injected directly into dermal, adipose, skeletal, muscular, and ocular/intra-ocular tissue. Finally, the present hydrogel solution can be used as a secondary inert biocompatible filler inserted into a secondary flexible container, such as a balloon, catheter, or other similar container before or after implantation. For example, a balloon comprised of a silicone, urethane or other flexible polymer "skin" our layer, and filled with the polymer of this invention to expand it to the desired space, prior to or after implantation. The terms "styrene maleic acid," "acid" and "styrene maleic acid copolymer" are used interchangeably for a styrene maleic acid polymer composition containing at least 70% maleic acid residues. Likewise, the terms "styrene maleic anhydride," "anhydride" and "styrene maleic anhydride copolymer" are also used herein interchangeably with one another for a styrene maleic anhydride polymer composition containing at least 30% anhydride residues. The reference to percentage of acid or anhydride is intended to mean that with respect to the maleic acid or anhydride monomers incorporated into the polymer chains, that percentage (or greater or lesser as indicated in the text) is hydrated to the acid form or dehydrated to the anhydrous form (in the finished product when formulated and filled into a pharmaceutical container) in the final product claimed here. This can include average percentage within the ranges or the average resulting from a mix of chains of differing percentages. All citations to percentages should be understood as being within customary formulation, analytical precision and accuracy limits. The expression "extravasating," which is used herein to define a characteristic of a solution solvent/carrier, is intended to mean that feature of such a solvent/carrier which causes it to flow away and disappear in the context of contact with anatomical tissue. DMSO is an appropriate extravasating solvent/carrier as it is a biocompatible, inert solvent for the polymer, is readily obtained in pharmaceutical (United States Pharmacopeia) grades, has a history of safe use in humans for this purpose, and in vivo easily diffuses through the vasa walls into the body tissue, where upon being replaced by the body water results in the gelation of the acid polymer. The present anatomical, hydrogel-forming solution may take on several, different, unique compositional forms, each useful in different circumstances, and each featuring a hydrogel-forming copolymer solute (styrene maleic acid solely, or such acid predominantly in a cooperative combination with styrene maleic anhydride) dissolved in a solvent which extravasates rapidly in the environment of, and through, the anatomy to "free" the solute to gelate in place to form the intended hydrogel tissue bridge. This hydrogel tissue bridge is one which may later be removed, if desired, through appropriate solvent dissolution and/or flushing. The present hydrogel tissue bridge can be stable in acidic pH, according to an embodiment. Therefore, the injection and/or flushing of a lumen containing the hydrogel tissue bridge with basic buffers like bicarbonate or phosphate and/or other similar alkaline agents can destabilize the hydrogel and disrupt the hydrogel tissue bridge, permitting removal of the polymer and flow out of the lumen of the vas deferens and similar anatomical structures.

The function of a hydrogel tissue bridge probably relates to the length of the vas deferens filled by the hydrogel. Since the diameter of the lumen of the vas deferens varies from person to person, if a fixed amount of material is injected, the length of the hydrogel tissue bridge will vary inversely with the square of the radius of the lumen of the vas deferens. In an embodiment, greater than 1 cm of the lumen of the vas deferens should be filled (occluded) with hydrogel tissue bridge in order to act as an effective contraceptive. The durability and effectiveness of the hydrogel tissue bridge will likely increase as the length of the hydrogel tissue bridge increases, with target lengths in the range of 4 to 20 cm in some embodiments.

According to the present embodiment, the composition of the proposed hydrogel-forming solution fundamentally takes two different overall forms. The first form features nearly pure styrene maleic acid (i.e., at least 90% acid) copolymer dissolved in DMSO or a similarly appropriate extravasating solvent/carrier. In this case, the DMSO may have a small quantity of residual water (not more than 5% by weight) without materially altering its quality by hydrolysis on storage. The second form features a blend of styrene maleic acid and styrene maleic anhydride copolymers dissolved in DMSO or a similarly appropriate extravasating solvent/carrier. In this second form, styrene maleic acid is the dominating copolymer, meaning the polymer has at least 75% acid residues. The use of dry DMSO (residual water of not more than 1% by weight) and filling of the formulated gel into a final container under dry nitrogen can be used to prevent excessive hydrolysis during storage. In either embodiment, the ratio of polymer to DMSO can range from 18% to 40% (wt/wt), wherein 22-26% (wt/wt) can be more preferable in some embodiments.

Regarding the acid-only form of the hydrogel-forming solution, the molecular weight of the acid therein preferably lies somewhere in the range of from above 100-kDa to about 1200-kDa. Keeping the molecular weight of the polymer within this range can assure that it will have sufficient viscosity to hold a desired position on injection so that it can fill the lumen during gelation, while still being capable of being handled in production, filled into vials and syringes, and being easily injectable when dissolved in DMSO. Higher molecular weights can be too viscous, while lower weights can be too fluid and flow out of vasa or spread excessively, thus not forming optimal plugs on gelation. The mass-fraction of the solution lies preferably somewhere in the range of about 15-percent to about 40-percent to provide an effective concentration of polymer for a specified injection volume. Lower concentrations may not form stable, strong plugs or have the same effect as low molecular weights on viscosity. Higher concentrations would have excessive viscosity for handling and injection. Various sub-ranges exist within these two broader ranges of molecular weights, as set forth specifically below. These sub-ranges can have properties which make them more useful when used for particular applications. Specifically, the particular molecular-weight and mass-fraction values deemed to be especially useful in many male-contraception applications are 200-1000 kDa, 300-800 kDa, 400-700 kDa, and 600-700 kDa to provide adequate features at concentrations of 18-40% (wt/wt) respectively. In an embodiment, a polymer of at least 95% acid, with molecular weight of 500-700 kDa at 23-26% (wt/wt) (polymer: DMSO concentration) can be used to create a suitable hydrogel tissue bridge in the vas deferens.

With respect to the acid/anhydride form of the solution, two preferred ratios by weight of acid to anhydride have been found to be interesting and useful in the different subforms of this solution, expressed in fuller detail below are 80%:20% and greater than 92% to less than 8%, and as noted above, preferably greater than 98% acid will function as a contraceptive agent. The lower acid level may provide improved (lower) viscosity for handling and a firm gel on injection. However, these benefits can be offset by hydrolysis of the anhydride, which can result in reduced stability, the inability to ensure consistent ratios of acid:anhydride residues upon final formulation, and difficulties in filling and injection due to the higher risk of hydrolysis during processing and filling as well as atmospheric moisture absorbed into the formulation.

The present styrene maleic acid polymer is predominately a linear polymer chain of styrene and maleic acid having minimal intermolecular or intramolecular cross-links, and generally intended and produced to have a poly (styrene-alt-maleic acid) form, rather than to have extended blocks of a single residue. Generally intended and produced means that at least 80% chain sequence is styrene-alt-maleic acid (as shown below) rather than styrene-styrene or other sequences. In addition the composition may be modified with small amounts of other residues or side groups that do not materially impair its principal contraceptive or occlusive function.

In a series of embodiments, the percentage of intermolecular or intramolecular cross-links in the styrene maleic acid polymer can be less than one percent (<1%), less than five percent (<5%), or less than ten percent (<10%). In an embodiment, the majority, more than ninety percent (>90%) of the linear chain can be made up of styrene-maleic acid copolymer blocks rather than styrene-styrene or maleic acid-maleic acid copolymer blocks. Cross-links are unfavorable as they provide variable properties (e.g., firmness, gelation, dissolution) that would need to be characterized and controlled.

As relates to male contraception, the hydrogel tissue bridge can be used to create a full or partial blockage, also referred to as an occluder of the vas deferens. This blockage can provide a relatively long-term and selectively reversible contraceptive. The present hydrogel-forming solutions can flow freely into small spaces creating a hydrogel tissue bridge that can remain flexible and stable, thus providing an occlusion of the vas deferens. This injectable male contraceptive solution can thus avoid some of the surgical invasiveness of the conventional vasectomy procedure. Another advantage over the prior art is that the present occlusion-forming solution can be easily removed, by way of a flushing mechanism and procedure, thus avoiding the invasiveness of a conventional vasovasostomy.

An occlusion formed by use of the present solution does not necessarily prevent the flow of all liquids through a lumen, in the sense that as a hydrogel fluids and subcellular small molecules can percolate through the matrix. This is distinguished form Guha's teachings that a non-occlusive polymer has open channels through which fluids and suspended cells, including sperms, can readily flow but are inactivated due to the polymer chemical effect on charge and pH. Quite importantly, the semisolid elastic/resilient nature of the acid plug, prevents the formation of stable side channels around the polymer, internal channels through the polymer, and pressure driven flow around the plug, through which sperm can pass. This is in contrast to the polymer taught by Guha, as well as the solid (e.g., silicon, EVA) and rigid (e.g., metal, polyethylene) plugs in prior teachings regarding contraceptives located within the vas deferens. Accordingly, such an occlusion can allow some amount of biological (seminal) fluids to pass through the occluding structure, referred to herein variously as a hydrogel bridge thus reducing the risk of buildup of epididymal and testicular pressure, which are both potential side effects of the traditional vasectomy.

Figure 1A:
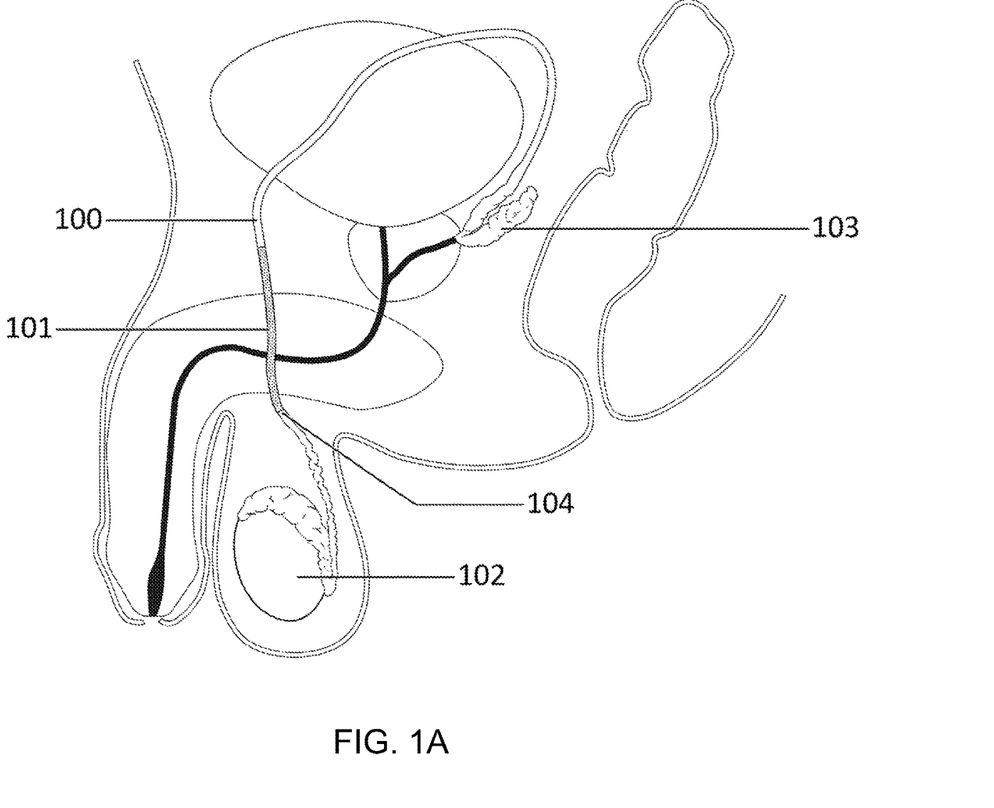
FIG. 1A is a representational diagram showing relevant parts of the human anatomy, including the vas deferens and the approximate location of a hydrogel tissue bridge within the vas deferens according to an embodiment.

FIG. 1A is a representational diagram showing relevant parts of the human anatomy, including the vas deferens 100 and the approximate location of a hydrogel tissue bridge 101 within the lumen of the vas deferens 100. Specifically, FIG. 1A shows a testis 102 having a vas deferens 100 connecting the testis to the seminal vesicle 103. FIG. 1A also shows an insertion point 104 through which the present hydrogel solution can be injected to form the hydrogel tissue bridge 101 in order to occlude the vas deferens 100, according to an embodiment.

Figure 1B:
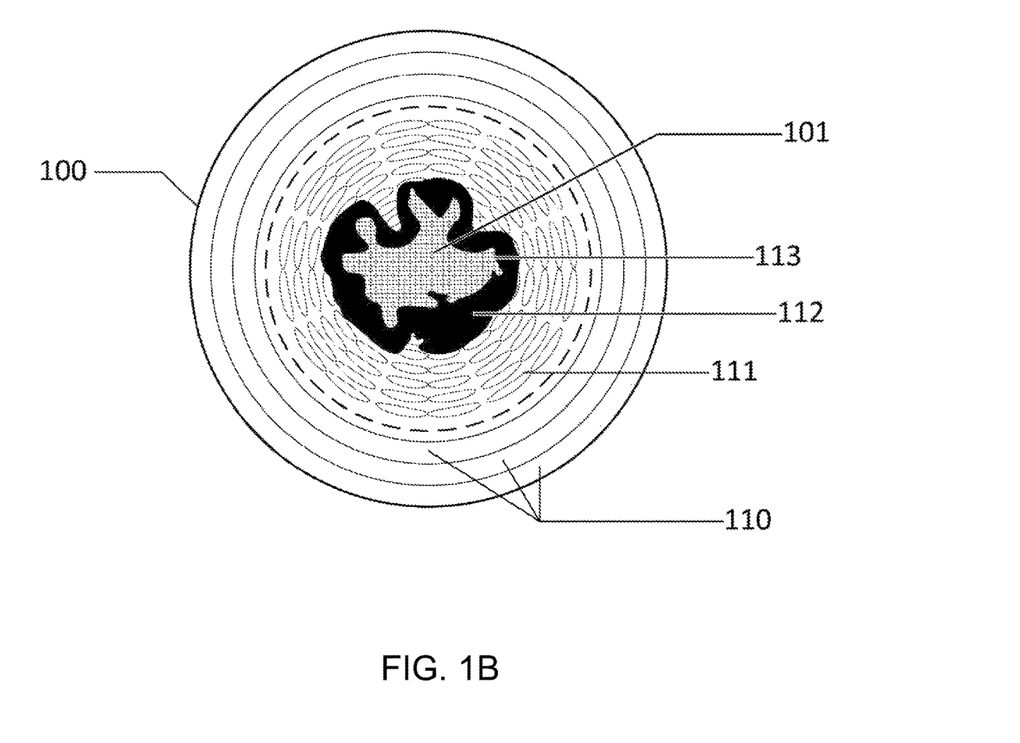
FIG. 1B is a cross-sectional view of a section of a vas deferens occluded by a hydrogel tissue bridge, also known as an occluder, as shown in FIG. 1A according to an embodiment.

FIG. 1B is a cross-sectional view of a section of the vas deferens 100 occluded by a hydrogel tissue bridge 101, also known as an occluder, as also shown in FIG. 1A according to an embodiment. FIG. 1B shows the various parts of the vas deferens 100, its circular, smooth muscle fibers 110, its longitudinal, smooth muscle fibers 111, and its epithelium 112, including a representation of its uneven surface 113. In this figure, the hydrogel tissue bridge 101 is shown to fill the lumen of the vas deferens 100 and form in and around the epithelium's uneven surface 113 creating a full blockage of the lumen of the vas deferens 100, thus preventing the passage of sperm (not shown) through it, according to an embodiment.

Solution Synthesis

In very general terms, solution synthesis, according to the presently disclosed compositions and methods, uniquely features in its early stage, the preparation of styrene maleic anhydride, the collaborative and cooperative employment of (a) ethyl acetate as a solvent, blended, and otherwise processed initially, with selected amounts of styrene and maleic anhydride, followed by (b) non-radiation, free-radical initiation implemented using benzoyl peroxide as the initiator.

This cooperative, early-stage use of ethyl acetate as a solvent and benzoyl peroxide as a free-radical initiator plays a significant role in offering a synthesis approach, according to the presently disclosed compositions and methods, which enables the mid-synthesis creation of a styrene maleic acid solute component possessing an easily controlled and achieved molecular weight range. In particular, this method for creating a styrene maleic acid solute component has been shown to provide excellent control and allow for the achievement of relatively large molecular weights, a consideration which has been determined to be important in many applications, such as in male contraceptive applications. It is via the employment of benzoyl peroxide as a free-radical initiator, and specifically by controlling the relative amount of benzoyl peroxide used for this purpose in the anhydride synthesis step, which offers such important control over the establishment of a desired range of styrene maleic acid molecular weights, and establishing it selectively at high molecular weights, such as those above 100-kDa.

Moreover, the present solvent/free-radical-initiation (ethyl-acetate/benzoyl-peroxide) processing approach, when used in relation to the styrene-maleic-anhydride creating step in the overall solution synthesis, is readily scalable, enabling the scalability of the overall solution-preparation, thus allowing for commercial-scale solution production.

Following the present solvent/free-radical-initiating procedure, in a concluding portion of the styrene-maleic-anhydride-forming part of the proposed synthesis, an acetone-processing step is included which functions as a purifying step that sets the stage for a final solute preparation of a near 100-percent styrene maleic acid to be blended into a solvent/carrier, such as DMSO.

The present solution-syntheses are fully described immediately below, including the preparation of nearly pure styrene maleic acid from the prepared styrene maleic anhydride, and subsequent appropriate blending of this acid into the intended solution solvent, such as DMSO. This detailed description of the present solution synthesis relates to the creation of a hydrogel-forming solution which is suitable for use as a male contraceptive as well as other useful hydrogel tissue bridges.

The following synthesis is provided as a specific example, and measurements of the weights, temperatures and volumes relate specifically to this example. Furthermore, it should be understood that the specific weights, temperatures and volumes provided are merely representative of those found within the ranges of acceptable weights and volumes for each component of this synthesis and the reaction temperatures described for each part of the synthesis.

Figure 2:
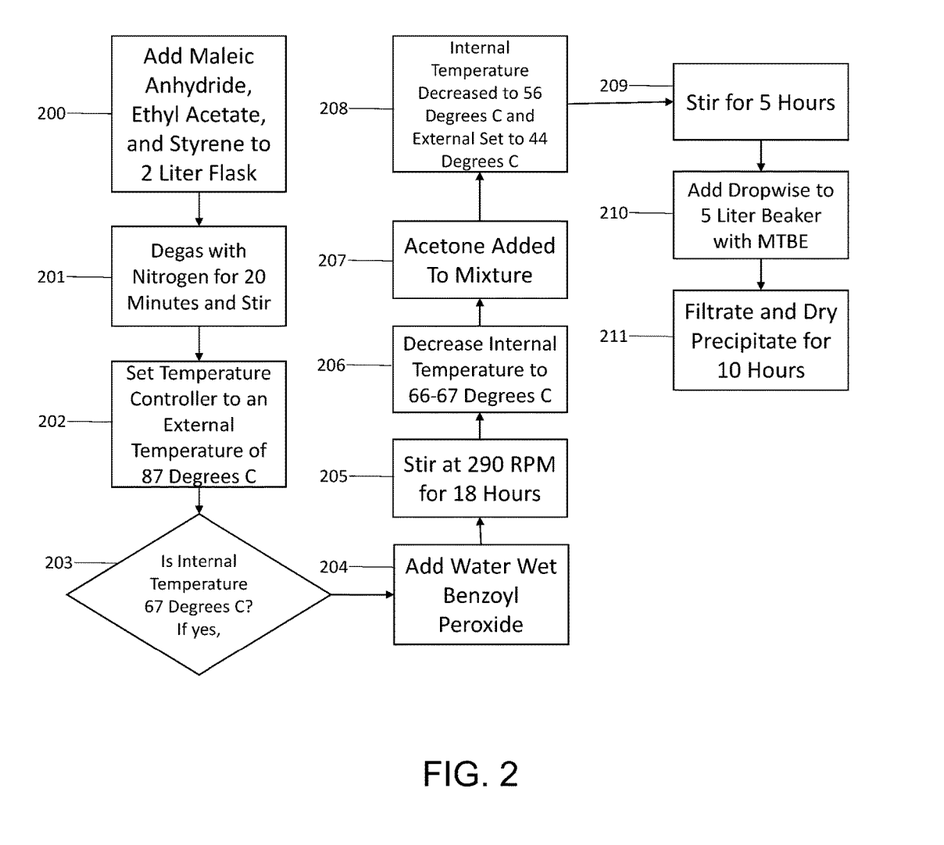
FIG. 2 is a flowchart showing the first steps of a synthesis of styrene maleic anhydride according to an embodiment.

Synthesis of Styrene Maleic Anhydride by Ethyl Acetate Precipitation and Benzoyl Peroxide Free-Radical Initiation The equipment used in the following synthesis can include a 2-L four-necked round-bottom flask, an overhead stirrer, a reflux condenser, a temperature probe and a glass tube connected to a dry nitrogen line. FIG. 2 is a flowchart showing the first steps of the following synthesis of styrene maleic anhydride. In FIG. 2, steps 200 thru 211 can be followed sequentially illustrating the steps of the synthesis of styrene maleic anhydride as described below. Table 1 lists the ingredients and amounts described in this section.

According to an embodiment, maleic anhydride (50-g, 0.51-mol), ethyl acetate (solvent) (500-ml), and styrene (45.37-g, 50-ml, 0.436 mol) can be placed into a 2-L four-necked round-bottom flask. The resulting mixture can then be degassed with nitrogen for twenty (20) minutes with the glass tube connected to a dry nitrogen line while stirring with the overhead stirrer, and while warming up with the heating mantle and temperature controller (J-probe, appropriately set at 40-60% to prevent wide temperature fluctuations) connected to the temperature probe, external temperature set at 87° C.

According to an embodiment, when the internal temperature reaches 66° C., 75% water wet benzoyl peroxide (initiator) (Luperox®, Aldrich, 0.93-g, 2.89-mmol, 0.66-mol % to styrene, 0.73-wt. %) can be added to the reaction mixture. The resulting mixture can then be stirred at 290-rpm for 18-hours using the overhead stirrer. The external temperature can then be reset to 74° C. wherein the internal temperature can increase to 73-74° C. within the first 2.5-hours, then decreased to 66-67° C. In an embodiment, the appearance of the reaction mixture can change from a clear solution to an opaque gel, partly stuck to the walls of the 2 L flask 101 and the overhead stirrer. The majority amount can be in ¾-inch to 1-inch chunks, allowing for adequate stirring.

To establish purification, 500-ml of acetone can be added to the resulting mixture and the internal temperature can be decreased to 56° C. The external temperature can then be reset to 44° C. and the reaction mixture can be stirred in these conditions for 5-hours in order to dissolve all visible chunks of the product. The resulting clear, light-pink homogenous viscous solution, about 1.06-L, can then be added drop-wise to a 5-L beaker with vigorously stirred tert-butyl methyl ether (MTBE), 3-L. The product, precipitated as off-white beads, can then be isolated by filtration, rinsed with MTBE, and dried in a vacuum desiccator for 10-hours.

Figure 3:
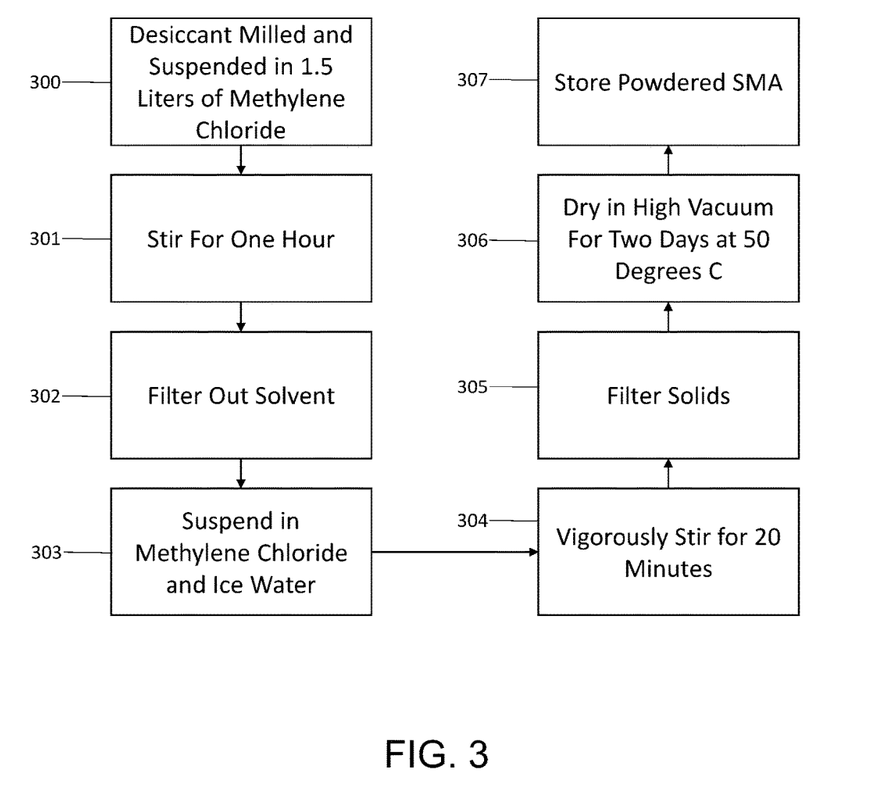
FIG. 3 is a flowchart showing further steps of a styrene maleic anhydride synthesis according to an embodiment.

FIG. 3 is a flowchart showing the following steps of the styrene maleic anhydride synthesis. In FIG. 3, steps 300 thru 307 can be followed sequentially illustrating the steps of the synthesis of styrene maleic anhydride as described below. The resulting crude product can then be milled and suspended in 1.5-L of methylene chloride. This suspension can then be stirred for an hour before filtering off the methylene chloride solvent. The wet cake can then be suspended in a mixture of methylene chloride (1 L) and ice-cold water (1-L) and vigorously stirred for 20-min. The solids can then be filtered and the aqueous layer of the filtrate can be analyzed with pH indicator paper. The measured pH should be approximately 4. The procedure can then be repeated two more times to achieve a pH in the range of 6-7 in the aqueous wash. After the last wash, the wet cake can then be thoroughly squeezed on the filter and dried in high vacuum at 50° C. for two days to give, as a dry powder, 82.5-g, 93.7%, of pure poly(styrene-co-maleic anhydride); Mw (Da) 628, 257, according to an embodiment.

TABLE 1

| Anhydride | Ingredient | Amount |
| --- | --- | --- |
| — | Maleic Anhydride | 50 g, 0.51 mol |
| — | Ethyl Acetate | 500 ml |
| — | Styrene | 43.37 g, 50-ml, 0.426 mol |
| — | 75% water wet benzoyl peroxide | 0.93 g, 2.89 mmol |
| — | Acetone | 500 ml |
| Dropwise to | Tert-butyl methyl ether | 3 L |
| Suspended in | Methylene chloride | — |

Synthesis of Styrene Maleic Acid by Base Hydrolysis of Anhydride in Water

Figure 4:
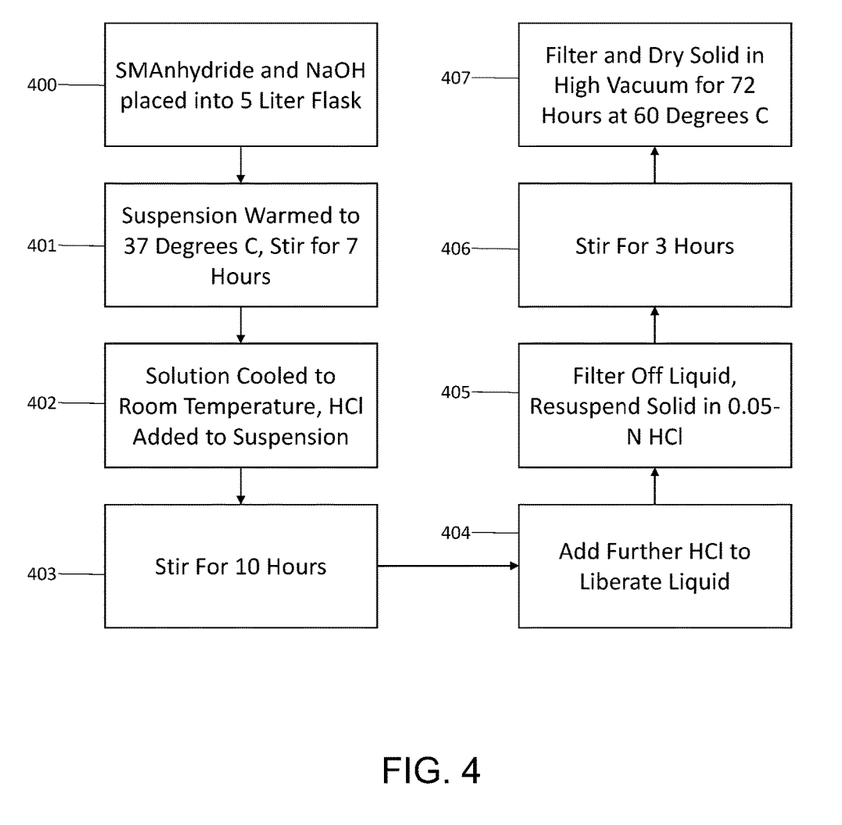
FIG. 4 is a flowchart showing the steps of a hydrolysis of styrene maleic anhydride, according to an embodiment.
Figure 5:
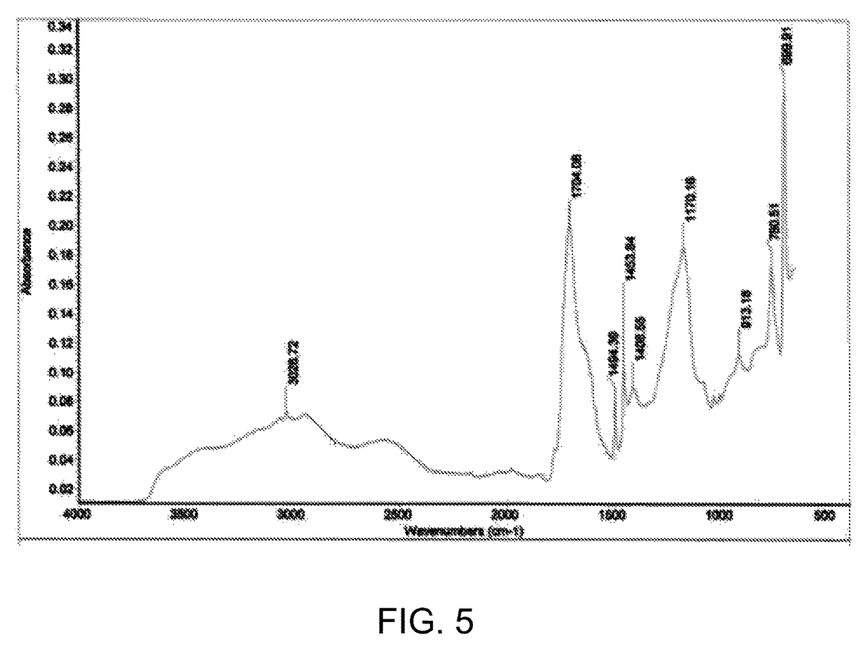
FIG. 5 is a representative Fourier Transform Infrared (FTIR) spectrum of styrene maleic acid.

FIG. 4 is a flowchart showing the following steps of the hydrolysis of styrene maleic anhydride, according to an embodiment. In FIG. 4, steps 400 thru 407 are followed sequentially illustrating the steps of the hydrolysis of styrene maleic anhydride as described below. According to an embodiment, styrene maleic anhydride (56-g, Mw 333,332), and in 1-N NaOH, 1.5-L, can be placed into a 5-L three-necked round-bottom flask with an overhead stirrer and a temperature probe. The formed suspension can then be warmed up to 37° C. (external temperature initially set at 57° C., them lowered to 44° C.) and stirred at that temperature for 7-hours to create a clear viscous solution. This solution can then be cooled down to room temperature and slowly acidified with 1-N HCl, which can be added in 250-ml portions. After addition of 1.25-L of 1-N HCl, the reaction can produce a mixture of clear liquid and white precipitate, which can then be stirred for ten hours at room temperature resulting in the formation of a clear, homogenous, extremely viscous gel with a pH of 6±1.0 pH units. To the gel can be added 250-ml of 1-N HCl, which can break the gel into pieces and liberate the liquid, which can then be filtered off. The solids can then be re-suspended in 1-L of 0.05-N HCl and stirred for 3-hours. These solids can then be filtered and dried in high vacuum at 60° C. for 72-hours to result in a dry powder, 60.4-g, of nearly pure (>85%) poly(styrene-co-maleic acid); Mw (Da) 339,019. Completeness of hydrolysis can be confirmed by Fourier Transform Infrared Spectroscopy (FTIR). FIG. 5 is a representative FTIR spectrum of styrene maleic acid.

Synthesis of Each of (1) Styrene Maleic Acid/DMSO Solution and (2) Styrene Maleic Acid/Styrene Maleic Anhydride/DMSO Solution In an embodiment, 205-g of each of the two principal solution compositions of the present method—(1) styrene maleic acid/DMSO, and (2) styrene maleic acid/styrene maleic anhydride/DMSO—can be made as follows: Composition (1), dry-powder styrene maleic acid, 22.05-g, can be weighed out into a 250-cc amber vial; Composition (2), dry-powder styrene maleic acid, 17.64-g, and dry styrene maleic anhydride, 4.41-g, can be weighed out into a 250-cc amber vial (Sartorius analytical balance CPA1003P was used). The vials with the dry mixtures can then be placed into a dry box together with an unopened Sure/Seal® capped bottle of anhydrous DMSO, a can opener, top loading balance Adam ADK-20, a glass beaker with two glass rods, glass funnel, and several sheets of aluminum foil.

In an embodiment, the dry box can be sealed, connected with a vacuum line and with a nitrogen line through a desiccator chamber. The air can then be vacuumed off and replaced with dry nitrogen five times. The DMSO bottle can then be opened inside the dry box, and to each amber vial can be added 82.95-g of DMSO. The resulting compositions can then be thoroughly mixed up with glass rods. The vials with the rods inside can then be covered with aluminum foil and kept in the dry box at room temperature. According to an embodiment, for the subsequent week, every day the mixtures can be stirred three or four times, resulting in lumps of solids gradually disappearing. After seven days, both master vials can contain uniform viscous turbid liquids—the intended, two, final solutions.

As an alternative to the terminal blending procedure described above, wherein final solution blending is performed by introducing liquid extravasating solvent, DMSO, into dry powder, a useful alternative involves a reverse approach featuring introducing the relevant dry powder into liquid extravasating solvent.

The above-elaborated synthesis descriptions present one set of specific ways in which the three principal stages of final solution formation, covering each of two, principal (wet DMSO) solution embodiments of the present method, may be carried out, and are believed to be clearly informative to those generally skilled in the relevant art regarding how to practice the synthesis methodology of the present method. In particular, the use, during polymerization of styrene maleic anhydride, of the uniquely combined steps involving the use of ethyl acetate as a solvent, and use of benzoyl peroxide as a free-radical (non-radiation) initiator are clearly described. In these presented synthesis stages, different molecular weights of solutes have been chosen to be discussed in order to show, representatively, a range in synthesis illustrations, with the understanding that a practitioner of the synthesis methodology may easily choose other styrene-maleic-acid molecular-weight values to be established, through controlling, appropriately, the relative amounts of benzoyl peroxide used in the anhydride synthesis step of the present method. It is this benzoyl-peroxide, amount-usage control which effectively determines final styrene maleic acid molecular weight.

Although the present methods and compositions have been described in terms of exemplary embodiments, none is limited thereto. Rather, the appended claims should be construed broadly, to include other variants and embodiments of the present methods and compositions, which may be made by those skilled in the art without departing from the scope and range of equivalents of either the compositions or the methods for using such compositions.

What is claimed is:

1. A hydrogel-forming solution comprising a polymer dissolved in a solvent, wherein the polymer is more than 75% comprised of styrene-alt-maleic acid and the solvent is DMSO, wherein the molecular weight of the polymer is within a range between 300 kDa and 800 kDa, and wherein the ratio of polymer to DMSO is within a weight/weight range from 15% to 40%.

2. The hydrogel forming solution of claim 1 wherein a percentage of intermolecular or intramolecular cross-links in the polymer is less than one percent.

3. The hydrogel forming solution of claim 1 wherein a percentage of intermolecular or intramolecular cross-links in the polymer is less than five percent.

4. The hydrogel forming solution of claim 1 wherein a percentage of intermolecular or intramolecular cross-links in the polymer is less than ten percent.

5. A method for creating a hydrogel tissue bridge within a space located within a subject, the method comprising:
providing a hydrogel-forming solution comprising a polymer dissolved in a solvent, wherein the polymer is more than 75% comprised of styrene-alt-maleic acid and the solvent is DMSO, wherein the molecular weight of the polymer is within a range between 300 kDa and 800 kDa, and wherein the ratio of polymer to DMSO is within a weight/weight range from 15% to 40%;
identifying a space within a subject comprising available water and aqueous solutions within the space; and
utilizing an injecting apparatus to place the hydrogel-forming solution within the space, wherein the hydrogel-forming solution absorbs the available water and aqueous solutions within the space thereby creating a hydrogel tissue bridge within the space.

6. The method as described in claim 5 wherein the space within a subject is the vas deferens.

7. The method as described in claim 5 wherein the injecting apparatus is a needle and syringe.

8. The method as described in claim 5 wherein the ratio of polymer to DMSO in the hydrogel-forming solution is within a weight/weight range from 15% to 40%.

9. The method as described in claim 5 wherein a percentage of intermolecular or intramolecular cross-links in the polymer is less than one percent.

10. The method as described in claim 5 wherein a percentage of intermolecular or intramolecular cross-links in the polymer is less than five percent.

11. The method as described in claim 5 wherein a percentage of intermolecular or intramolecular cross-links in the polymer is less than ten percent.

12. The method as described in claim 5 wherein the hydrogel tissue bridge is removed by injecting a basic bicarbonate buffer solution into the space within a subject with the injecting apparatus.

13. A method of preventing seminal fluid from comprising sperm cells, the method comprising:
providing a hydrogel-forming solution comprising a polymer dissolved in a solvent, wherein the polymer is more than 75% comprised of styrene-alt-maleic acid and the solvent is DMSO, wherein the molecular weight of the polymer is within a range between 300 kDa and 800 kDa, and wherein the ratio of polymer to DMSO is within a weight/weight range from 15% to 40%; and
utilizing an injecting apparatus to place the hydrogel-forming solution within a space, wherein the space is a vas deferens, and wherein the hydrogel-forming solution absorbs the water and aqueous solutions available within the vas deferens, creates a hydrogel tissue bridge within the vas deferens, and occludes said vas deferens, thereby preventing seminal fluid from comprising sperm cells.

14. The hydrogel-forming solution of claim 1, wherein the molecular weight of the polymer is within a range between 400 kDa and 700 kDa.

* * * * *